US008043365B2

(12) United States Patent
Thramann

(10) Patent No.: US 8,043,365 B2
(45) Date of Patent: Oct. 25, 2011

(54) METHODS FOR PLACEMENT OF VASCULAR STENT GRAFTS AND VASCULAR STENTS

(76) Inventor: Jeffery Thramann, Longmont, CO (US)

( * ) Notice: Subject to any disclaimer, the term of this patent is extended or adjusted under 35 U.S.C. 154(b) by 560 days.

(21) Appl. No.: 11/773,838

(22) Filed: Jul. 5, 2007

(65) Prior Publication Data

US 2008/0086193 A1    Apr. 10, 2008

Related U.S. Application Data

(63) Continuation-in-part of application No. 10/643,554, filed on Aug. 18, 2003, now abandoned.

(60) Provisional application No. 60/404,344, filed on Aug. 19, 2002, provisional application No. 60/404,343, filed on Aug. 19, 2002.

(51) Int. Cl.
*A61F 2/06* (2006.01)
(52) U.S. Cl. ...................................... 623/1.34
(58) Field of Classification Search ........ 623/1.13–1.22, 623/1.34–1.36; 128/898, 899
See application file for complete search history.

(56) References Cited

U.S. PATENT DOCUMENTS

| | | | | |
|---|---|---|---|---|
| 5,709,713 A * | 1/1998 | Evans et al. | .................. | 623/1.53 |
| 6,261,273 B1 * | 7/2001 | Ruiz | .............................. | 604/284 |
| 6,264,682 B1 * | 7/2001 | Wilson et al. | ................ | 623/1.11 |
| 6,652,567 B1 * | 11/2003 | Deaton | .......................... | 623/1.1 |
| 6,723,116 B2 * | 4/2004 | Taheri | .......................... | 623/1.11 |
| 6,827,736 B2 * | 12/2004 | Perouse | ....................... | 623/1.36 |
| 7,854,758 B2 * | 12/2010 | Taheri | .......................... | 623/1.23 |

* cited by examiner

*Primary Examiner* — Melanie Tyson
(74) *Attorney, Agent, or Firm* — Holland & Hart, LLP

(57) ABSTRACT

The present application provides a method of repairing a diseased vessel having a plurality of branch vessels extending therefrom. The method includes locating a vessel to removal from blood flow. A single incision is made to provide access to the vessel. Branch locating stent grafts having radio opaque edges are placed in a plurality of branch vessels branching from the located vessel. A single main vessel stent graft is placed in the vessel temporarily occlude the branch locating stent grafts that subsequently are located using the radio opaque edges. The surgeon punctures the wall of the main vessel stent graft at the edges to provide an access port from the main vessel stent graft to the branch locating stent grafts and finally places a plurality of branch connecting stents corresponding to each of the plurality of branch locating stent grafts.

3 Claims, 9 Drawing Sheets

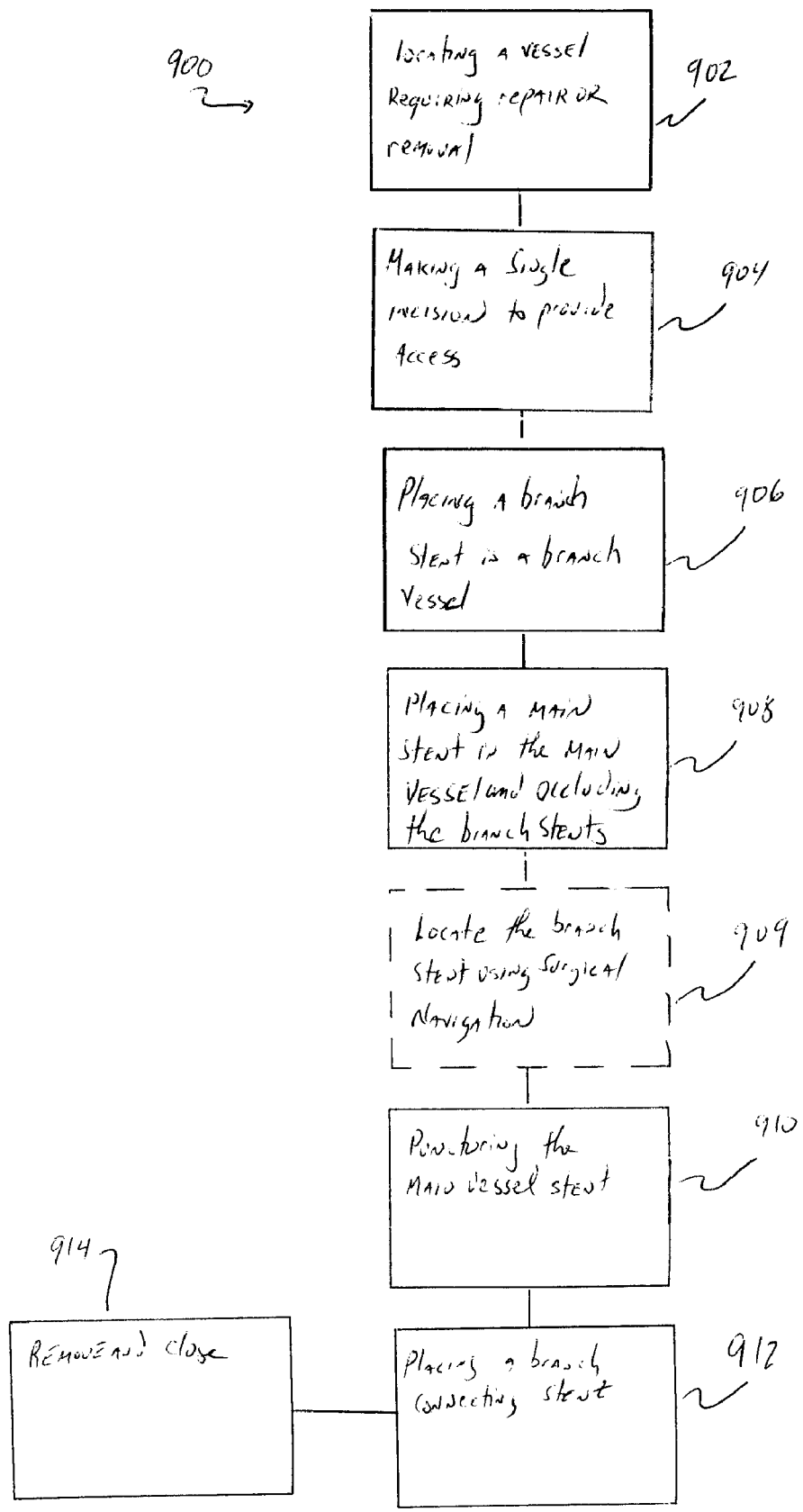

METHODS FOR PLACEMENT OF VASCULAR STENT GRAFTS AND VASCULAR STENTS

CLAIM OF PRIORITY UNDER 35 U.S.C. §§119 AND 120

The present Application for Patent is a Continuation in Part and claims priority to patent application Ser. No. 10/643,554 entitled "VASCULAR STENT GRAFTS" filed Aug. 18, 2003, abandoned, which is hereby expressly incorporated by reference herein, which claims priority to Provisional Patent Applications Nos. 60/404,343 and 60/404,344, filed Aug. 19, 2002, entitled "MODULAR RECONSTRUCTABLE ENDOVASCULAR BYPASS STENT GRAFT" and "MODULAR RECONSTRUCTABLE STENT GRAFT" which are hereby expressly incorporated by reference herein.

REFERENCE TO CO-PENDING APPLICATIONS FOR PATENT

None.

BACKGROUND

1. Field

The technology of the present application relates to vascular surgery and, more particularly, a methodology for using vascular stents grafts in bypassing or removing portions of vascular anatomy from circulation and/or reconstructing vascular anatomy.

2. Background

The circulatory system comprises many different parts, one of which is the vascular system. Blood vessels can develop various problems, diseases, or other pathology that frequently requires surgical repair.

Two common conditions include vascular blockage, such as, for example, blood clots, and aneurysms. Blockage is generally repaired surgically by, for example, bypass surgery, a balloon catheter, or the like. Surgeons conventionally treat aneurysms by surgically removing the aneurysm. Some aneurysms can be treated using endovascular methodologies including placing a stent graft, but frequently endovascular treatment using a stent graft is not possible because branch vessels become occluded. These and other conventional procedures for correcting vascular pathology are not particularly satisfactory. Thus, it would be desirous to develop apparatuses and methods that allowed for endovascular repair of the vascular system.

SUMMARY

To attain the advantages and in accordance with the purpose of the invention, as embodied and broadly described herein, methods to facilitate endovascular repair of a diseased vessel are provided. In particular, the method comprises locating a main vessel of the endovascular system that requires repair. Making a single incision to allow access to the main vessel. Placing a branch locating stent graft having a radio opaque marker in a branch vessel located off of a main vessel. Placing a main vessel stent graft in the located main vessel such that the branch locating stent graft is occluded. Locating the branch locating stent graft using the radio opaque marker. Puncturing a wall of the main vessel stent graft at the located radio opaque marker to provide an access port from the main vessel stent graft to the branch locating stent graft and providing a branch connecting stent from the main vessel stent graft to the branch locating stent graft such that the main vessel stent graft, the branch connecting stent, and the branch locating stent graft are in fluid communication.

The foregoing and other features, utilities, and advantages of the technology of the present application will be apparent from the following more particular description of exemplary embodiments as illustrated in the accompanying drawings.

BRIEF DESCRIPTION OF THE DRAWINGS

The accompanying drawings, which are incorporated in and constitute a part of this specification, illustrate embodiments of the technology of the present application, and together with the descriptions, serve to explain the principles thereof. Like items in the drawings may be referred to using the same numerical reference.

FIG. 9 shows an illustrative flow chart describing a method of implanting stents consistent with the technology of the present application.

DETAILED DESCRIPTION

Some embodiments of the present invention are described with reference to FIGS. 1 to 9. The embodiments are described with reference to exemplary embodiments thereof. The word "exemplary" is used herein to mean "serving as an example, instance, or illustration." Any embodiment described herein as "exemplary" is not necessarily to be construed as preferred or advantageous over other embodiments. Moreover, unless otherwise stated, all embodiments described herein should be construed as exemplary.

Figure 1:
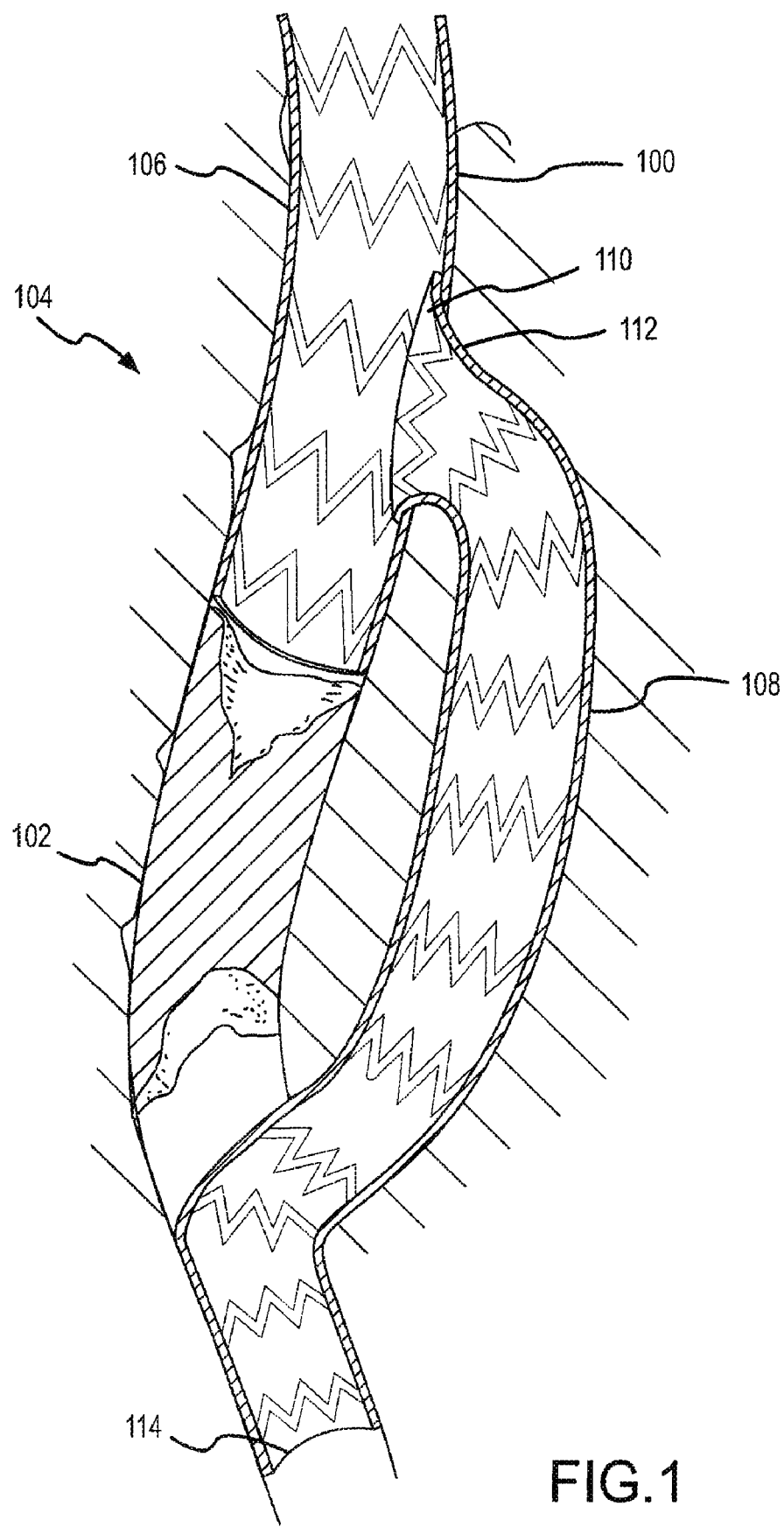
FIG. 1 shows a portion of a vascular anatomy with an endovascular stent graft consistent with the technology of the present application.

Referring first to FIG. 1, a cut-away portion of a blood vessel 100 is shown. A clot 102, blockage, or other vascular pathology in blood vessel 100 requires a bypass. An endovascular bypass stent graft 104 is shown implanted in blood vessel 100. Endovascular bypass stent graft 104 comprises a main vessel stent graft 106 and a bypass stent graft 108. Main vessel stent graft 106 has an access port 110 located proximate clot 102. Bypass stent graft 108 has a proximate end 112 and a distal end 114. Proximate end 112 is connected to access port 110 in a sealing relationship, which will be explained further below with respect to FIG. 4. Distal end 114 resides within vessel 100 such that bypass stent graft 108 bypasses clot 102 or other vascular pathology.

Figure 2:
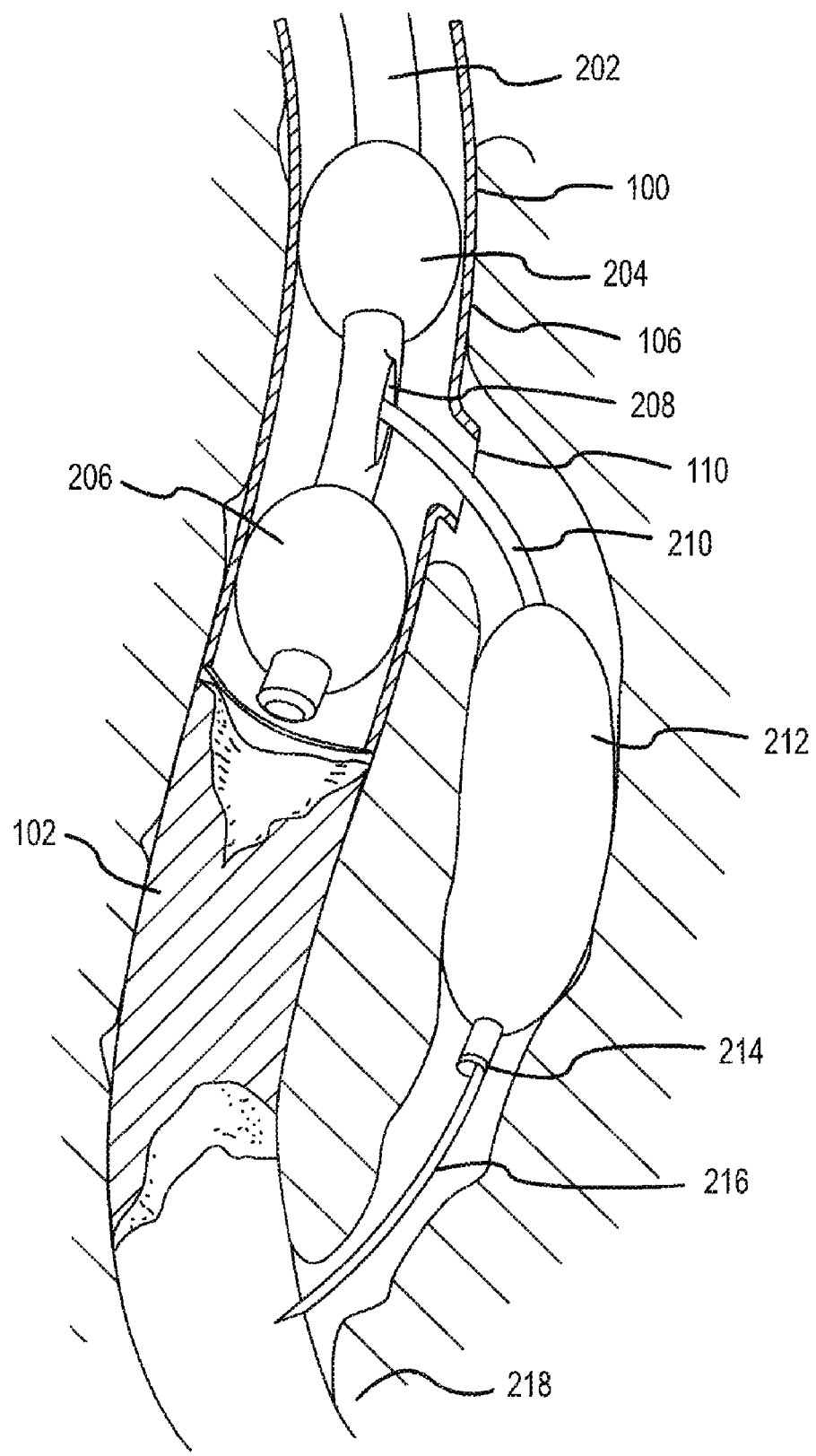
FIG. 2 shows devices useful for placement of the endovascular stent graft of FIG. 1.

Implanting or deploying endovascular bypass stent graft 104 will be explained with reference to FIG. 2. First a main deployment catheter 202 and main vessel stent graft 106 are guided to clot 102 using standard endovascular surgical techniques. Main deployment catheter 202 comprises a proximate balloon 204, a distal balloon 206, and a working port 208. Inflating proximate balloon 204 and distal balloon 206 isolates working port 208 from blood flow.

Figure 3:
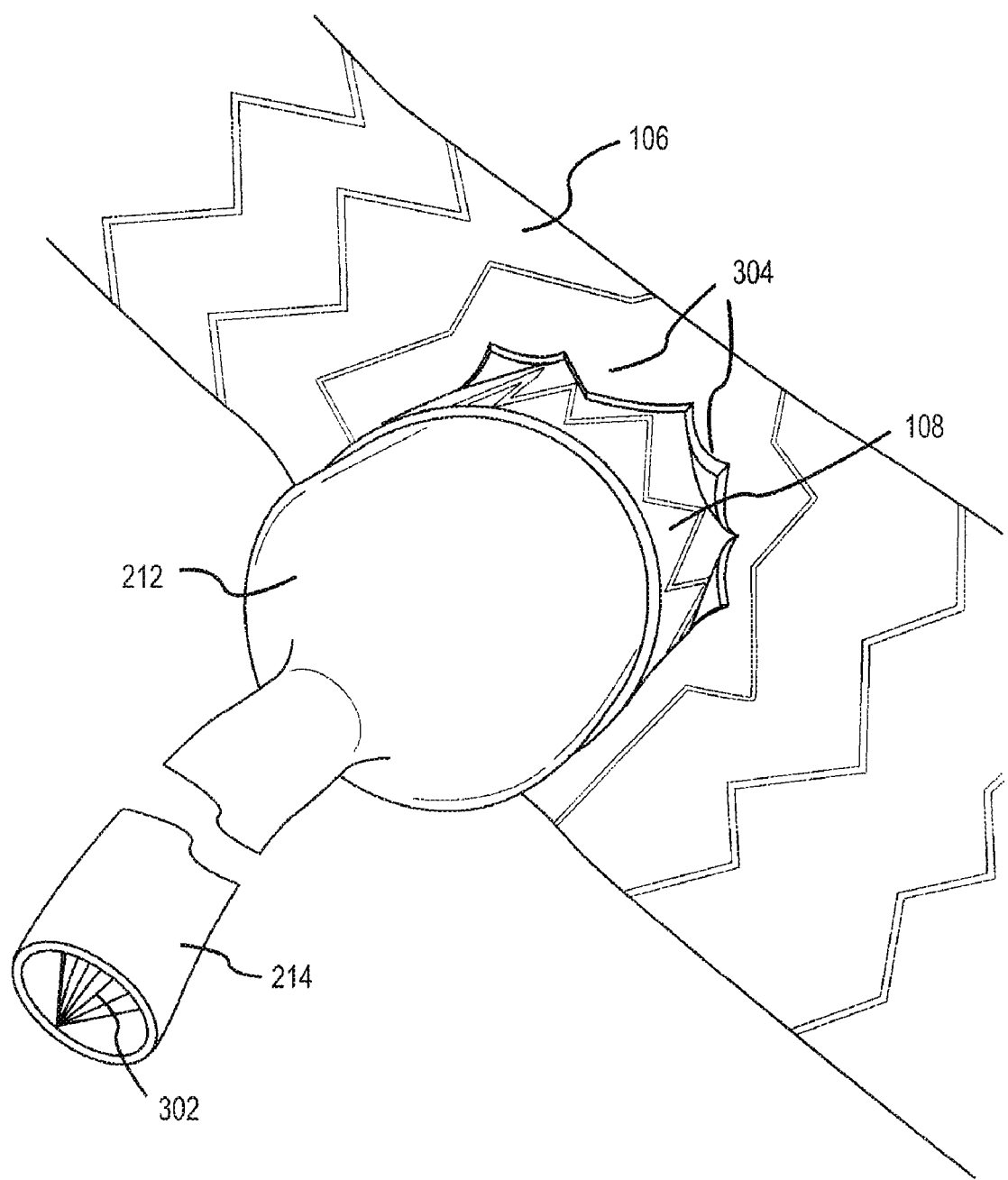
FIG. 3 shows puncturing a main vessel stent graft consistent with establishing a working port.

Referring now to FIG. 3, a trocar 302 is passed through the main deployment catheter 202 and out working port 208 once balloons 204 and 206 isolate blood flow. Using 3-D navigational technology (as is commonly available in the art), trocar 302 is aligned with working port 208 and used to puncture main blood vessel 100 about working port 208. As shown in FIG. 3, main vessel stent graft 106 may be deployed without an access port 110. In this case, trocar 302 first punctures main vessel stent graft 106 to make the access port 110. When the access port 110 in main vessel stent graft 106 is made by trocar 302, main vessel stent graft 106 is designed to form a controlled tear pattern, such as a controlled stellate pattern 304, as is commonly known in the art.

Once blood vessel 100 is punctured, a bypass catheter 210 is passed to the vascular pathology and through working port 208 to access port 110. Bypass catheter 210 comprises a dissecting balloon 212 and a tool port 214 at the distal end thereof. A wire needle 216 is passed out tool port 214. Using the bypass catheter 210, dissecting balloon 212 and wire needle 216 pass through the working port 208, access port 110, and the puncture of blood vessel 100 and enters the perivascular space about blood vessel 100. The dissecting balloon dissects the perivascular space up to a vessel re-entry port 218. Vessel re-entry port 218 is shown as a part of blood vessel 100 such that clot 102 is removed from circulation, but vessel re-entry port 218 could reside in a separate blood vessel (not specifically shown) as required by the patient's anatomy and the particular pathology involved. Wire needle 216 punctures the vessel to establish re-entry port 218.

Once wire needle 216 establishes re-entry port 218, bypass catheter 210 is removed and bypass stent graft 108 is passed over wire needle 216. Distal end 114 is placed in the vessel at re-entry port 218 and expanded to fit snuggly with the vessel wall in a sealing relationship. Bypass stent graft 108 could be expanded using a balloon or made out of an expanding material, such as, for example, shape memory alloys. The proximate end 112 and access port 110 are joined in a sealing relationship, as explained below.

Once bypass stem graft 108 is placed, proximate balloon 204 is deflated and blood flow is verified. Finally, distal balloon 206 is deflated and the catheter is removed leaving endovascular bypass stent graft 104 in place.

Figure 4:
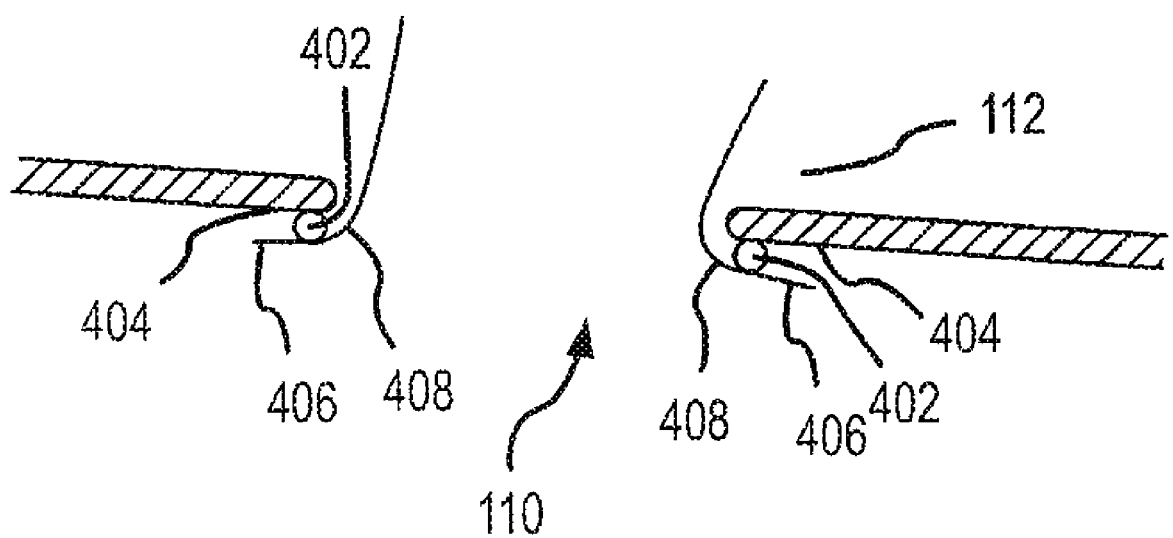
FIG. 4 shows a cross-sectional view of an access port and bypass stent graft consistent with an embodiment of the technology of the present application.

FIG. 4 shows the sealing relationship between access port 110 and proximate end 112 in more detail. In particular, a cross-sectional view of access port 110 and proximate end 112 is shown. Access port 110 has an edge 402 defining access port 110. About edge 402 is a seating surface 404. Proximate end 112 has a corresponding engaging surface 406. Engaging surface 406 mates with seating surface 404 to forma seal that inhibits blood leakage. Reference number 408 is a material that further inhibits bleeding or leakage. Reference number 408 could be a sealing ring, such as a GOR-TEX® washer, that could be deployed between seating surface 404 and engaging surface 406 to further inhibit blood flow. Alternatively, reference number 408 could be a form of epoxy, acrylic, silicone, tape, glue, or resin that seals seating surface 404 and engaging surface 406. Still further, bypass stent graft 108 and/or main vessel stent graft 102 could be constructed out of shape memory alloys, such as, for example, Ag—Cd alloys, Cu—Al—Ni alloys, Cu—Sn alloys, Cu—Zn alloys, Cu—Zn—Si alloys, Cu—Zn—Sn alloys, Cu—Zn—Al alloys, In—Ti alloys, Ni—Al alloys, Ni—Ti alloys, Fe—Pt alloys, Mn—Cu alloys, Fe—Mn—Si alloys, and the like. These could be designed such that seating surface 404 and engaging surface 406 form an adequate seal and then deformed for deployment. After deployment, an activation signal could cause seating surface 404 and engaging surface 406 to join in a sealing relationship. The activation signal could be a thermal, electrical, magnetic, radiation signal or the like. Notice, the seal between access port 110 and bypass stem graft 108 could be accomplished using a branch connecting stent. Branch connecting stents are explained further below with reference to FIG. 7.

Figure 5:
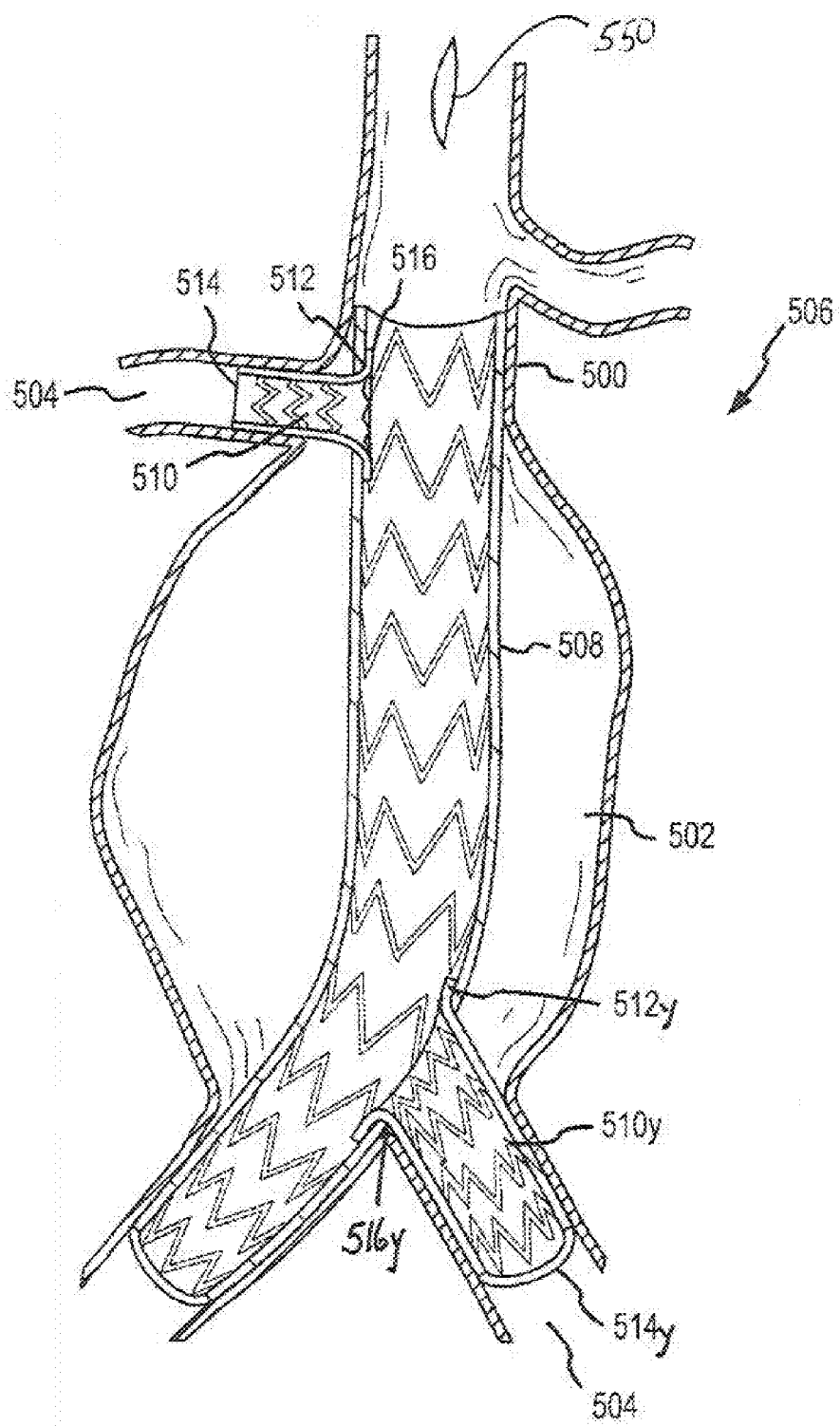
FIG. 5 shows a portion of a vascular anatomy with an endovascular stent graft consistent with another embodiment of the technology of the present application.
Figure 6:
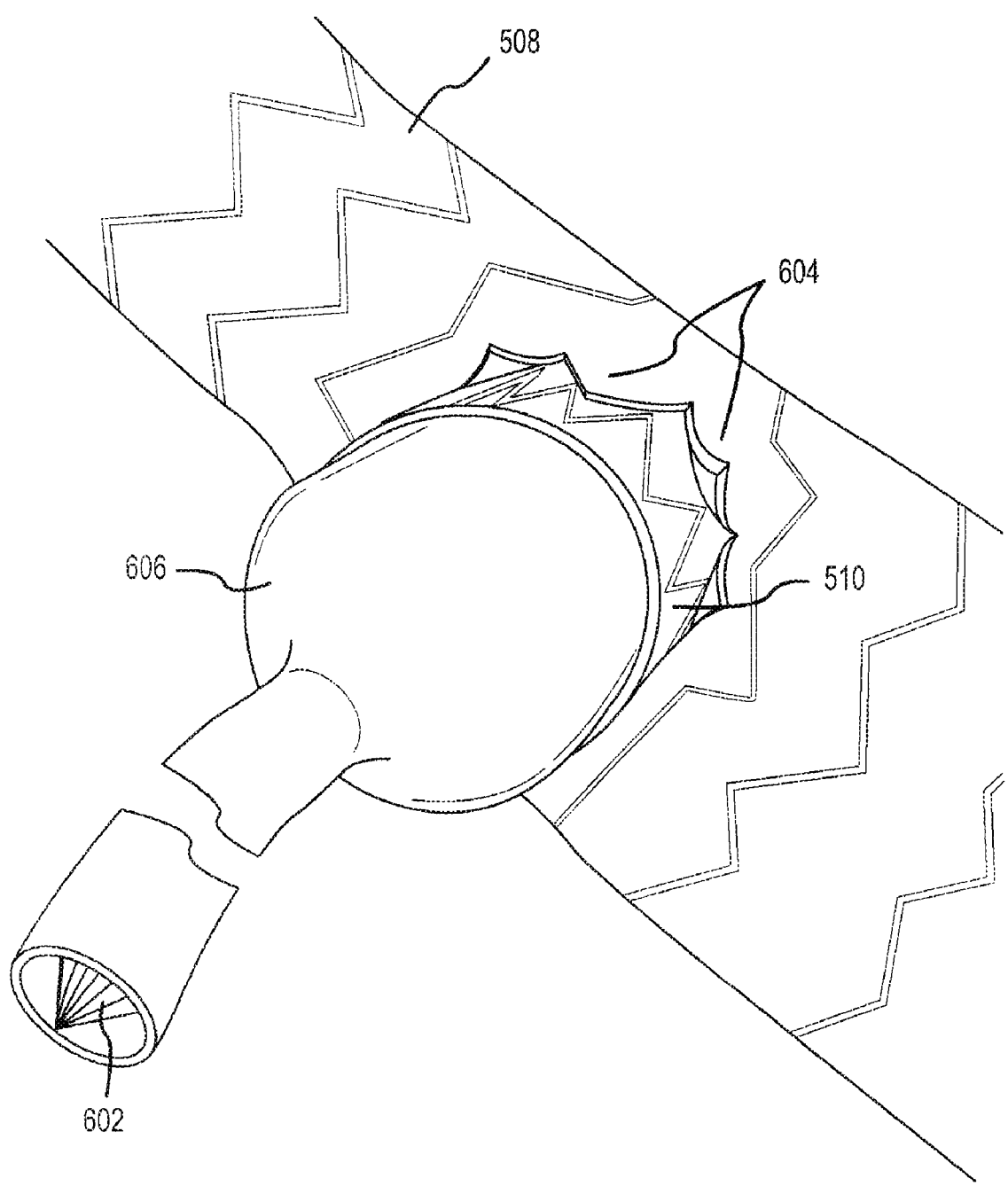
FIG. 6 shows puncturing a main vessel stent graft consistent with establishing a working port.

Referring now to FIG. 5, another embodiment of the present invention is shown. FIG. 5 shows a cut-away portion of a blood vessel 500. In this case, blood vessel 500 contains a type of aneurysm 502 or other vascular pathology that needs to be isolated from blood vessel 500. As shown, blood vessel 500 has branch vessels 504 that prevent the use of a conventional stent because a conventional stent would occlude blood flow to branch vessels 504 indefinitely. In this case, endovascular stent graft 506 includes a main vessel stent graft 508 and a number of branch connecting stents 510, 510y. Branch connecting stent 510y is similar to branch connecting stent 510, but is distinguished to illustrate the use of a Y shaped main vessel stent 800 in place of main vessel stent 508 as is explained further below in connection with FIG. 8. In this case, two branch connecting stents 510 and 510y are shown, but more or less could be deployed as necessitated by patient anatomy. Branch connecting stents 510, 510y connect through access ports 512, 512y to main vessel stent graft 508 such that distal ends 514, 514y of branch connecting stems 510, 510y reside in branch vessels 504 and proximate ends 516, 516y of branch connecting stents 510, 510y are in a sealing relationship with access ports 512, 512y, such sealing relationship is further explained in connection with FIGS. 4 and 7.

Endovascular stent graft 506 can be deployed in a number of different ways. For example, main vessel stent graft 508 can be placed using conventional endovascular techniques. Once placed, using 3-D surgical navigation techniques, commonly known in the art, a trocar 602 is used to puncture main vessel stent graft 508 at the junction with branch vessel 504 (See FIG. 6). Main vessel stent graft 508 is constructed such that trocar 602 would form a controlled tear 604, such as a controlled stellate pattern. A balloon 606 would be used to dilate tear 604 to a size capable of accepting branch connecting stents 510, 510y. Branch connecting stents 510, 510y are then passed to the site such that distal ends 514, 514y reside in branch vessels 504 and proximate ends 516, 516y form a sealing relationship with access ports 512, 512y.

While main vessel stent graft 508 (and main vessel stent graft 106) is shown as a tubular member conforming to the shape of the vessel 500 (or 100), main vessel stent graft 508 could be other shapes, such as, for example, a y shaped main vessel stent graft 800. In this case, y branch 802 would replace branch connecting stent 510y (FIG. 5) as well as remove the need for access port 512y. Other shapes are possible.

Figure 7:
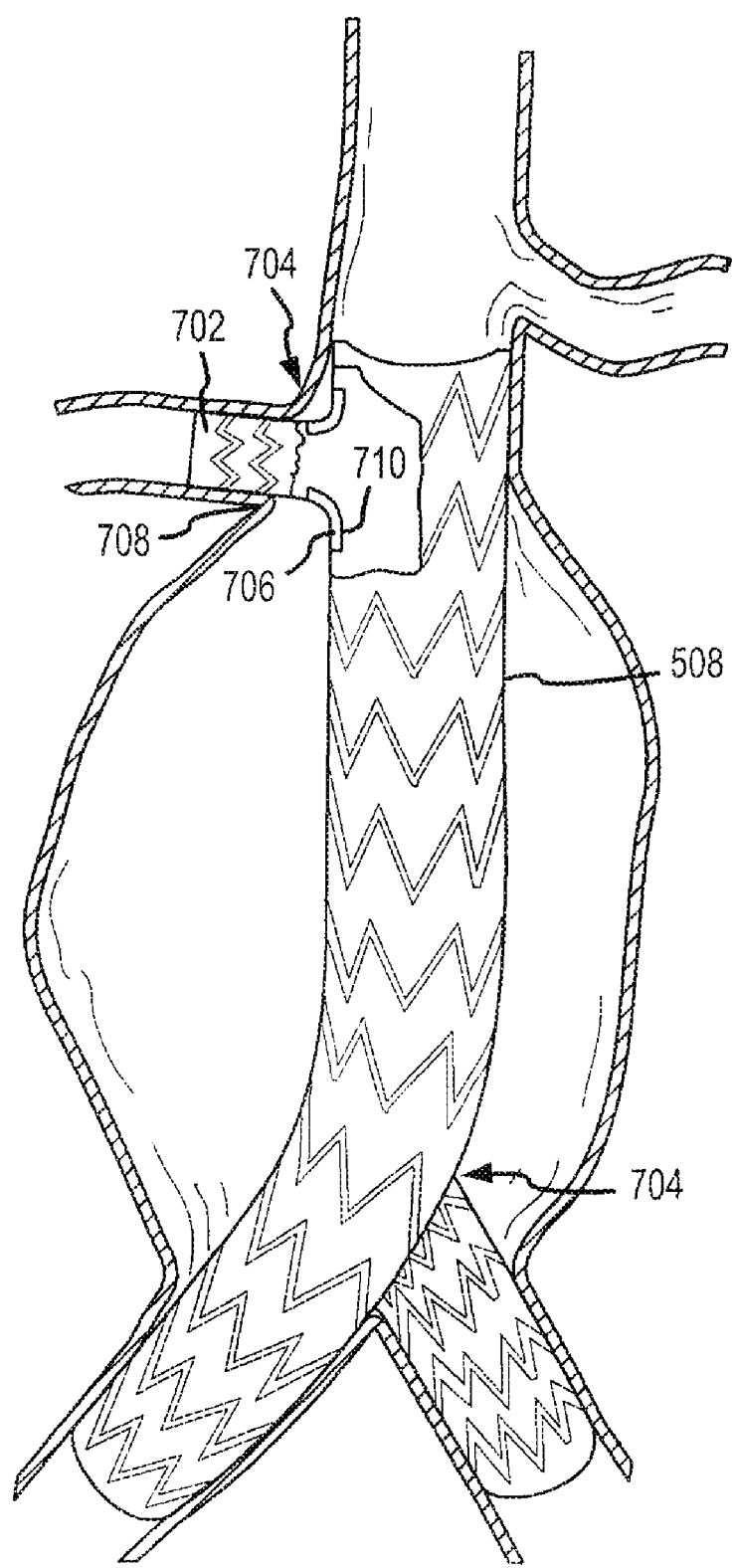
FIG. 7 shows a portion of a vascular anatomy with an endovascular stent graft consistent with another embodiment of the technology of the present application.
Figure 8:
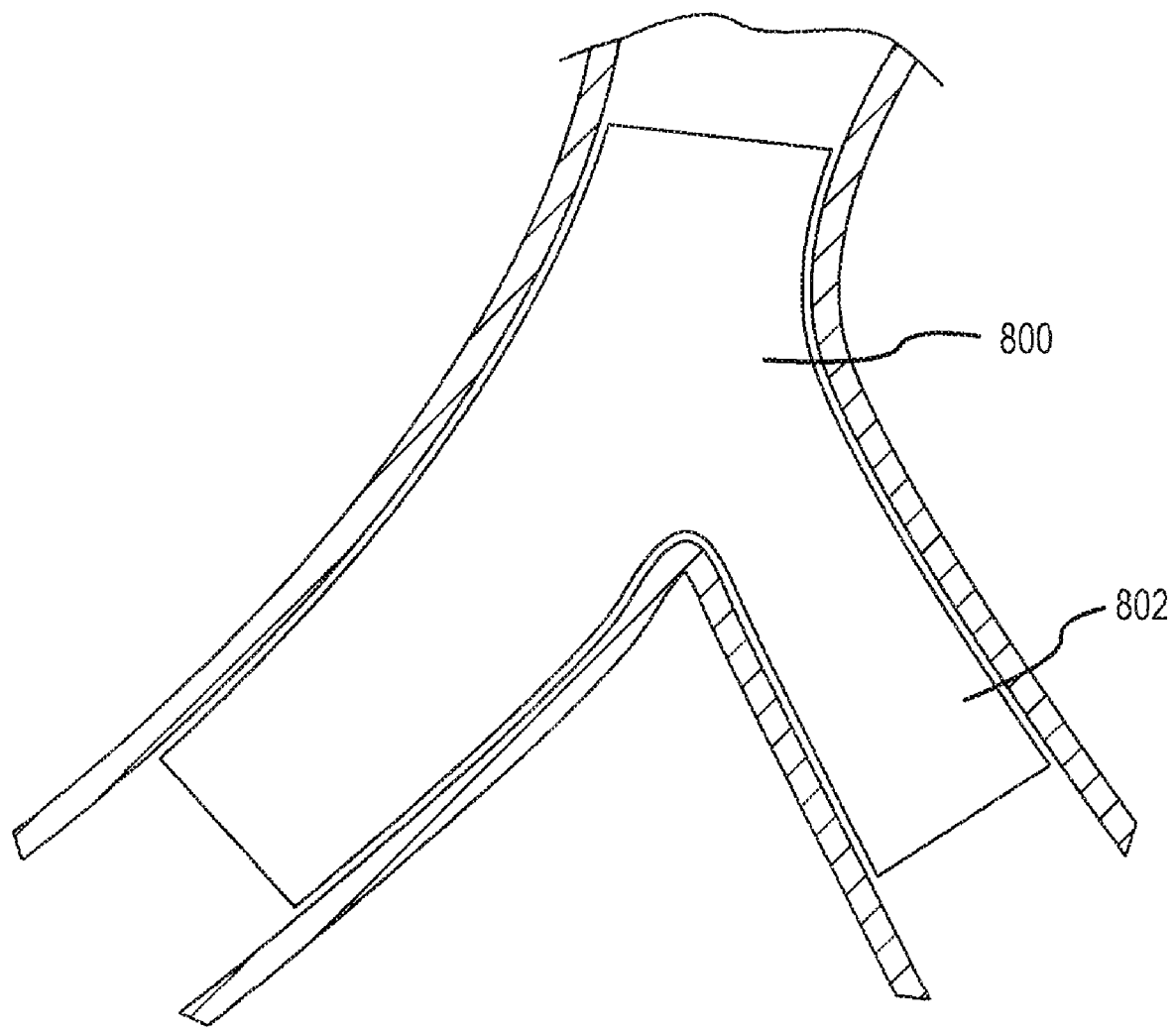
FIG. 8 shows another construction of main vessel stent graft.

FIG. 7 shows placing branch locating stent graft 702. Branch locating stent graft 702 would have a radiopaque edge 704 proximate vessel 500. Main vessel stent graft 508 would be passed to the vascular site occluding branch vessels 504 and branch locating stent graft 702. Trocar 604 would then be aligned with radio opaque edge 704 using 3D surgical navigation as is commonly understood in the art or some other conventional mechanism and main vessel stent graft 508 would be punctured to form access port 512. A branch connecting stent 706 would then be placed such that a distal end 708 of branch connecting stent 706 resided in and formed a sealing relationship with branch locating stent graft 702 and a proximate end 710 of branch connecting stent 706 resides in and forms a sealing relationship with access port 512 of main vessel stent graft 508.

Referring now to FIG. 9, a flowchart 900 is provided illustrating an exemplary methodology associated with one or more of the stents described above. First, a surgeon would locate or identify a portion of the vascular system that required repair or removal from blood flow, step 902. For example, blood vessel 500 has aneurysm 502, see FIG. 5, or the like is identified by the surgeon. Next, a single incision is made in the endovascular system to provide surgical access to the blood vessel 500, step 904. For example, an incision 550 may be made in blood vessel 500, see FIG. 5. Using conventional surgical techniques, such as, for example, inserting a catheter through incision 550 to branch vessels, branch locating stents grafts 702 are placed in branch vessels 504 through the incision 550. Branch locating stents grafts are provided with radio opaque edges 704, step 906. Main vessel stem graft 508 is placed through the incision 550, step 908, following placement of branch locating stents grafts 702 using conventional surgical techniques. Main vessel stent graft 508 occludes branch locating stent grafts 702. Using surgical navigation equipment to locate the radio opaque edges, a trocar, or the like, punctures the wall of main vessel stent graft 508 to provide the access port 512 on the wall, steps 909 and 910. A branch connecting stent 706 is then provided to provide fluid communication between main vessel stent graft 508, branch connecting stent 706, and branch locating stents graft 702, step 912. Subsequently, the tools are removed and the incision closed, step 914.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A method for the repair of a diseased vessel having a plurality of branch vessels comprising the steps of:
   locating a vessel of the endovascular system that requires removal from blood flow;
   making a single incision into the endovascular system to provide access to the located vessel;
   placing via the single incision a plurality of branch locating stent grafts each having a radio opaque edge in a corresponding plurality of branch vessels branching from the located vessel;
   placing via the single incision a single main vessel stent graft in the located vessel temporarily occluding the plurality of branch locating stent grafts;
   locating the radio opaque edge of the plurality of branch locating stent grafts;
   puncturing a wall of the main vessel stent graft at the located radio opaque edges of the plurality of branch locating stent grafts to provide an access port from the main vessel stent graft to each of the plurality of branch locating stent grafts; and
   placing via the single incision a plurality of branch connecting stents corresponding to each of the plurality of branch locating stent grafts such that the main vessel stent graft, the plurality of branch connecting stents, and the plurality of branch locating stent grafts are in fluid communication.

2. The method of claim 1, wherein the step of puncturing the wall includes tearing the wall of the main vessel stent graft in a controlled pattern to form the access port.

3. The method of claim 2, wherein the access port includes an edge and a seating surface about the edge and the method further comprises expanding the branch connecting stent to form a sealing relationship with the seating surface.

\* \* \* \* \*